United States Patent
Bourne

(10) Patent No.: US 10,278,861 B2
(45) Date of Patent: May 7, 2019

(54) PHACOEMULSIFICATION HANDPIECE WITH FLEXIBLE IMPELLER PUMP

(71) Applicant: NOVARTIS AG, Basel (CH)

(72) Inventor: John Morgan Bourne, Irvine, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/218,995

(22) Filed: Jul. 25, 2016

(65) Prior Publication Data

US 2017/0367885 A1    Dec. 28, 2017

Related U.S. Application Data

(60) Provisional application No. 62/354,265, filed on Jun. 24, 2016.

(51) Int. Cl.
*A61F 9/007* (2006.01)
*A61M 1/00* (2006.01)

(52) U.S. Cl.
CPC ....... *A61F 9/00745* (2013.01); *A61M 1/0031* (2013.01); *A61M 1/0064* (2013.01); *A61M 1/0066* (2013.01); *A61M 2205/0216* (2013.01); *A61M 2205/3344* (2013.01); *A61M 2210/0612* (2013.01)

(58) Field of Classification Search
CPC .. A61F 9/00745; A61F 9/00763; A61F 9/013; A61B 2017/00685; A61M 1/0031; A61M 1/0064; A61M 1/0066; A61M 2205/0216; A61M 2205/3344; A61M 2210/0612
See application file for complete search history.

(56) References Cited

U.S. PATENT DOCUMENTS

| | | | |
|---|---|---|---|
| 6,506,176 B1 * | 1/2003 | Mittelstein | A61F 9/00763 604/107 |
| 2011/0137231 A1 | 6/2011 | Sorensen et al. | |
| 2011/0144567 A1 | 6/2011 | Sorensen et al. | |
| 2012/0083728 A1 | 4/2012 | Sorensen et al. | |
| 2013/0046228 A1 | 2/2013 | Bourne | |
| 2014/0163454 A1 | 6/2014 | Sussman et al. | |
| 2014/0271251 A1 * | 9/2014 | Bourne | F04B 43/12 417/53 |
| 2014/0271273 A1 | 9/2014 | Carpenter | |
| 2014/0276364 A1 | 9/2014 | Sussman | |
| 2015/0125328 A1 | 5/2015 | Bourne et al. | |
| 2015/0157501 A1 | 6/2015 | Bourne et al. | |

(Continued)

FOREIGN PATENT DOCUMENTS

| | | |
|---|---|---|
| AU | 2004202819 | 7/2004 |
| WO | 0215828 A2 | 2/2002 |

(Continued)

*Primary Examiner* — Brandy S Lee

(57) ABSTRACT

A phacoemulsification system that includes a hand-graspable body and a phacoemulsification needle extending from a distal portion of the body is disclosed herein. The phacoemulsification system may also include an impeller pump carried by the hand-graspable body and configured to convey an aspiration fluid from a surgical site. The impeller pump may include an aspiration motor and a flexible impeller coupled to and rotatably driven by the aspiration motor. The flexible impeller may be arranged to aspirate fluid and emulsified lens tissue from the surgical site.

16 Claims, 5 Drawing Sheets

(56) References Cited

U.S. PATENT DOCUMENTS

2015/0297405 A1   10/2015  Bourne et al.
2015/0359666 A1*  12/2015  Zacharias .......... A61F 9/00736
                                                     604/500

FOREIGN PATENT DOCUMENTS

WO      09076717 A1   6/2009
WO      15069445 A1   5/2015

* cited by examiner

PHACOEMULSIFICATION HANDPIECE WITH FLEXIBLE IMPELLER PUMP

CROSS REFERENCE TO RELATED APPLICATIONS

This application claims the benefit of U.S. Provisional Application No. 62/354,265, filed Jun. 24, 2016, the contents being incorporated herein by reference.

TECHNICAL FIELD

The devices, systems, and methods disclosed herein relate generally to phacoemulsification surgery.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. A typical surgical handpiece used for phacoemulsification procedures includes of an ultrasonically driven cutting needle surrounded by an irrigating sleeve and is attached to an electronic control surgical system. The handpiece is attached to the control surgical system by an electric cable and flexible conduit. Through the electric cable, the surgical system varies the power level transmitted by the handpiece to the attached cutting needle. The flexible conduit supplies irrigation fluid to the surgical site and draws aspiration fluid from the eye through the handpiece assembly.

During the phacoemulsification procedure, the tip of the cutting needle and the end of the irrigation sleeve are inserted into the anterior segment of the eye through a small incision in the outer tissue of the eye. The surgeon brings the tip of the cutting needle into contact with the lens of the eye, and the vibrating tip fragments the lens. The resulting fragments are aspirated out of the eye through the interior bore of the cutting needle and transported to a drain reservoir.

A common complication during the phacoemulsification process arises from a blockage or occlusion of the aspirating needle. As the irrigation fluid and emulsified tissue are aspirated away from the interior of the eye through the hollow cutting needle, fragments of tissue that are larger than the diameter of the needle's bore may become clogged in the needle's tip. While the tip is clogged, vacuum pressure builds up within the aspiration conduit, including lumen of the cutting needle. Once the occlusion is cleared, a surge of fluid is removed from the eye due to a vacuum formed within the aspiration conduit. The resulting drop in pressure in the anterior chamber in the eye when the occlusion is removed is known as post-occlusion surge. This post-occlusion surge can, in some cases, cause a relatively large quantity of fluid and tissue to be aspirated out of the eye too quickly, potentially causing the eye to collapse and/or causing the lens capsule to be torn.

SUMMARY

The present disclosure relates generally to devices, systems, and methods for pumping an aspiration fluid from a surgical site during an ophthalmic procedure using a flexible impeller pump integrated with a phacoemulsification handpiece.

Exemplary systems are provided herein. An exemplary phacoemulsification system may include a hand-graspable body and a phacoemulsification needle extending from a distal portion of the body. The phacoemulsification needle may be arranged to ultrasonically vibrate to treat an ocular condition. The phacoemulsification system may also include an ultrasonic vibration generator cooperatively coupled to and arranged to vibrate the phacoemulsification needle. The phacoemulsification needle may be ultrasonically vibratable in response to a vibration of the ultrasonic vibration generator. An impeller pump may be carried by the hand-graspable body and may be configured to convey an aspiration fluid from a surgical site. The impeller pump may include an aspiration motor and a flexible impeller coupled to and rotatably driven by the aspiration motor. The flexible impeller may be arranged to aspirate fluid and emulsified lens tissue from the surgical site.

The flexible impeller may include a plurality of radially extending vanes. Each of the plurality of radially extending vanes may include a bulbous tip. The vanes may be radially spaced apart within a range of 33 and 67 degrees. The impeller pump may include an impeller chamber. The impeller may be non-concentrically disposed within the impeller chamber. The impeller chamber may have a non-circular cross-section. The impeller chamber may include an inlet and an outlet extending at an angle from each other. The angle formed between the inlet and the outlet may be between 30 and 120 degrees. An access opening may be provided the hand-graspable body to provide selective access to the impeller pump. The flexible impeller may be removable from the body through the access opening. The impeller pump may include an inlet in fluid communication with the needle and an outlet in fluid communication with a connector disposed on the hand-graspable body. The phacoemulsification system may also include a sensor carried on the hand-graspable body and a controller in communication with the sensor. The controller may be configured to generate a pump control signal to control the impeller pump based on information sensed by the sensor.

According to another exemplary aspect, the present disclosure is directed to a phacoemulsification system for treating an ocular condition at a surgical site. The system may include a hand-graspable body and an irrigation system carried on the hand-graspable body. The irrigation system may convey an irrigation fluid for injection from a distal end of the hand-graspable body to the surgical site. An aspiration system may be carried on the hand-graspable body and may convey an aspiration fluid into the distal end of the hand-graspable body from the surgical site. The aspiration system may include an aspiration motor, an impeller chamber, and a flexible impeller. The flexible impeller may be rotatably disposed in the impeller chamber and coupled to and rotatably driven by the aspiration motor. The flexible impeller may be arranged to aspirate fluid and emulsified lens tissue from the surgical site.

The phacoemulsification system may also include a phacoemulsification needle extending from the distal portion of the body and arranged to ultrasonically vibrate to treat the ocular condition and an ultrasonic vibration generator cooperatively coupled to and arranged to vibrate the phacoemulsification needle. The flexible impeller may include a plurality of radially extending vanes. Each of the plurality of radially extending vanes may include a bulbous tip. The vanes may be radially spaced apart within a range of 30 and 70 degrees. The impeller chamber may have a non-circular cross-section. A sensor may be carried on the hand-graspable body. A controller may be in communication with the sensor and configured to generate a pump control signal to control the aspiration motor based on information sensed by the sensor.

According to yet another exemplary aspect, the present disclosure is directed to a phacoemulsification system that may include a hand-graspable body and a phacoemulsification needle. The needle may extend from a distal portion of the body and may be arranged to ultrasonically vibrate to treat an ocular condition. An ultrasonic vibration generator may be cooperatively coupled to and arranged to vibrate the phacoemulsification needle. The phacoemulsification needle may vibrate ultrasonically in response to a vibration of the ultrasonic vibration generator. An irrigation system may be carried on the hand-graspable body. The irrigation system may include a passageway to convey an irrigation fluid for injection from a distal end of the hand-graspable body to the surgical site. An aspiration system may be carried on the hand-graspable body. The aspiration system may include a conduit to convey an aspiration fluid into the distal end of the hand-graspable body from the surgical site. The aspiration system may include an aspiration motor, an impeller chamber, and a flexible impeller. The flexible impeller may be rotatably disposed in the impeller chamber and coupled to and rotatably driven by the aspiration motor. The flexible impeller may be arranged to aspirate fluid and emulsified lens tissue from the surgical site. The flexible impeller may include a plurality of radially extending vanes.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the accompanying drawings and the following detailed description.

BRIEF DESCRIPTION OF THE DRAWINGS

The accompanying drawings illustrate implementations of the devices and methods disclosed herein and together with the description, serve to explain the principles of the present disclosure.

Figure 1:
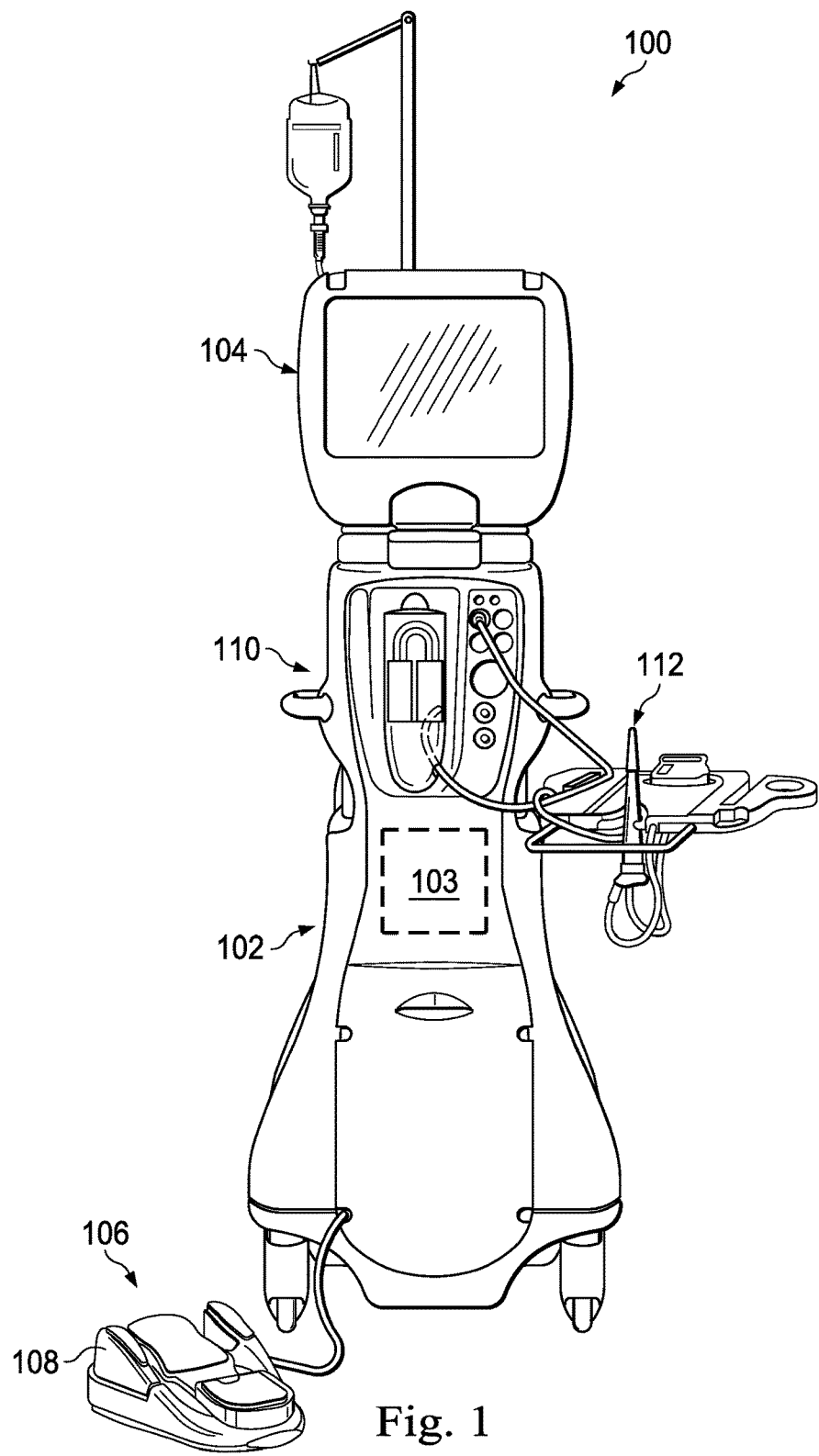
FIG. 1 illustrates an exemplary surgical system.

The accompanying drawings may be better understood by reference to the following detailed description.

DETAILED DESCRIPTION

For the purposes of promoting an understanding of the principles of the present disclosure, reference will now be made to the implementations illustrated in the drawings. Specific language will be used to describe the same. It will nevertheless be understood that no limitation of the scope of the disclosure is intended. Any alterations and further modifications to the described devices, systems, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure. For example, although explanatory references are made to "ophthalmic applications," other medical applications are included within the scope of the present disclosure. For simplicity, in some instances the same reference numbers are used throughout the drawings to refer to the same or like parts.

The present disclosure relates generally to devices, systems, and methods for pumping an aspiration fluid and tissue, such as lens fragments, from a surgical site during a phacoemulsification procedure. In some implementations, the devices, systems, and methods employ a flexible impeller pump integrated with a phacoemulsification handpiece. With the pump disposed on the handpiece, the devices, systems, and methods may provide responsive control of the aspiration fluid flow, minimizing occlusion surge and providing a consistent fluid flow. The flexible impeller pump may provide several advantages over alternative pumps usable in a phacoemulsification system. For example, a flexible impeller pump may deform or comply to lens fragments or other debris without affecting the operability of the pump and without damaging the pump. This may increase the life of the pump, as well as the effectiveness of the pump during a surgical procedure. As another example, a flexible impeller pump may be self-priming. This may provide efficiencies in the operating room because healthcare providers would not need to prime the pump prior to performing the surgery. In addition, the flexible impeller pump may be reversible. Accordingly, if needed, the flexible impeller pump may be used to reflux and dislodge occlusions at the phacoemulsification needle tip.

Figure 2:
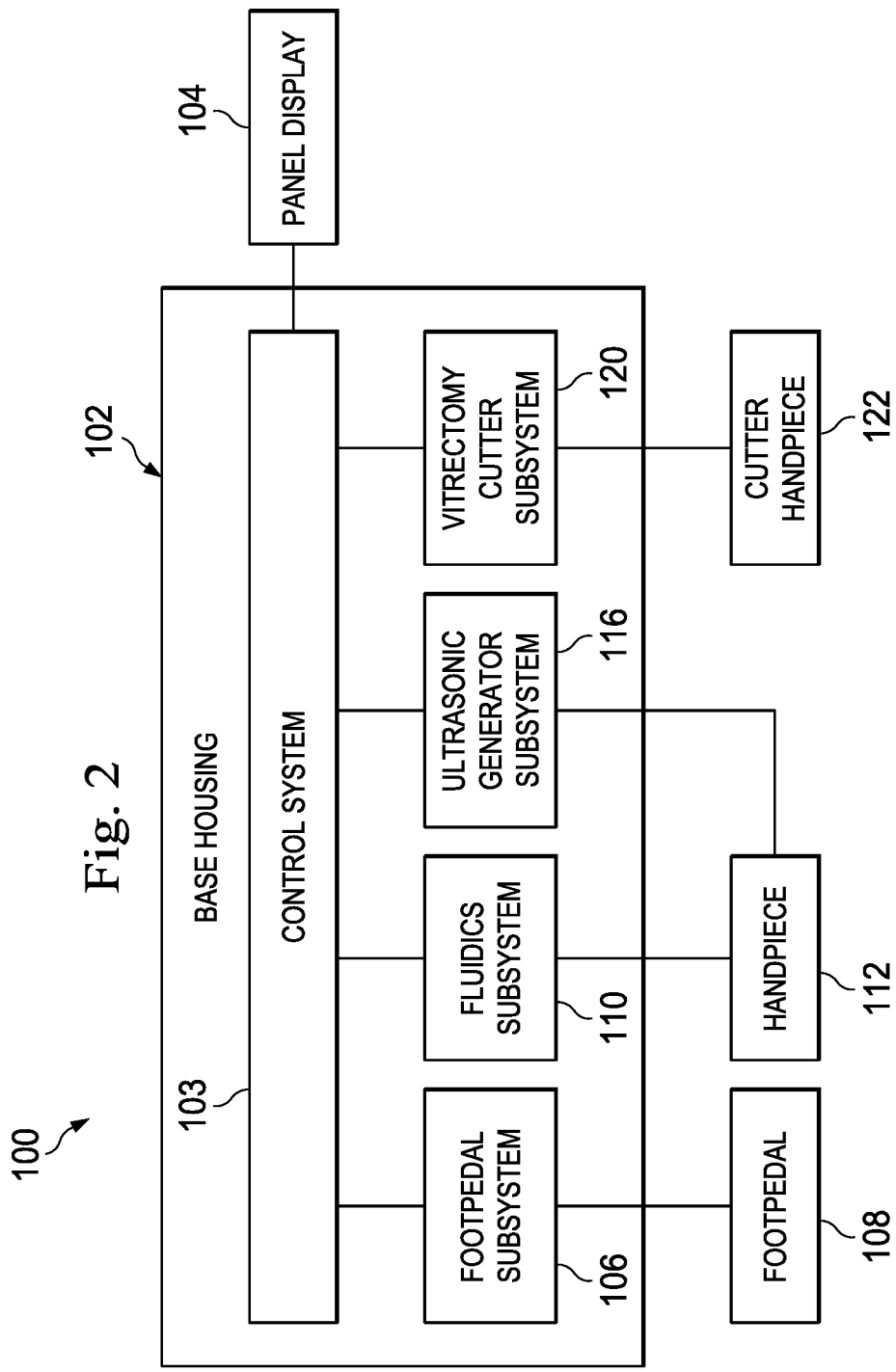
FIG. 2 is an illustration of an exemplary block diagram of the exemplary surgical system of FIG. 1.

FIG. 1 illustrates an exemplary emulsification surgical system, generally designated 100. FIG. 2 is a block diagram of the surgical system 100 showing various subsystems that operate to perform an ophthalmic procedure, such as a phacoemulsification procedure. The surgical system 100 includes a base housing 102 with a control system 103, an associated display screen 104 showing data relating to system operation and performance during a phacoemulsification surgical procedure, and a fluidics subsystem 110. The surgical system 100 also includes at least a part of a number of subsystems that are used together to perform an emulsification surgical procedure. Some of these subsystems include components or elements that are separable from or not disposed on the surgical system 100. Other subsystems or components or elements thereof may be incorporated into the surgical system 100.

For example, and with reference to FIG. 2, some example subsystems may include a footpedal subsystem 106 that includes, for example, a footpedal 108, a handpiece 112 with an integrated aspiration pump, an ultrasonic generator subsystem 116 that provides an ultrasonic oscillation to a cutting needle of the handpiece 112, and a pneumatic vitrectomy cutter subsystem 120 including a vitrectomy handpiece 122 (not shown in FIG. 1). The handpiece 112 is fluidly coupled to the fluidics subsystem 110. One or more of the subsystems may overlap and cooperate to perform various aspects of the procedure.

Figure 3:
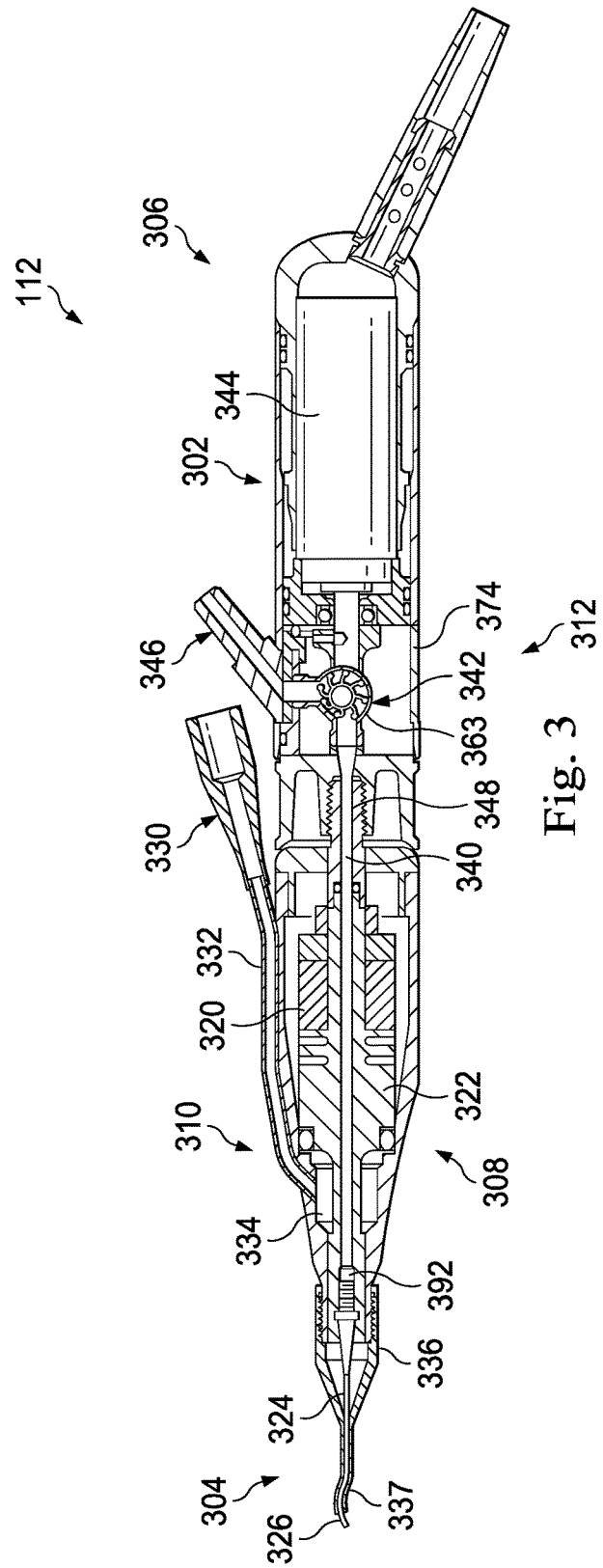
FIG. 3 is an illustration of a cross-sectional side view of an exemplary surgical instrument.

FIG. 3 is a cross-sectional view of the handpiece 112. The handpiece 112 may be arranged to perform a phacoemulsification procedure at a surgical site, such as a patient's eye. The handpiece 112 is sized to be grasped and manipulated by a user. The handpiece comprises a graspable body 302, a distal end 304, and a proximal end 306. Within or carried by the graspable body 302, the handpiece 112 also includes ultrasonic generator assembly 308, an irrigation system 310, and an aspiration system 312.

The ultrasonic generator assembly 308 may include an ultrasonic vibration generator 320, a horn 322, and a phacoemulsification needle 324. The ultrasonic vibration generator 320 may include a piezoelectric transducer, such as one or more piezoelectric crystals, or other components configured to generate ultrasonic vibration. In some implementations, the ultrasonic vibration generator 320 is in direct contact with the horn 322 and, when activated, may ultrasonically vibrate the horn 322. Similarly, the phacoemulsification needle 324 may be in direct contact with and carried by the horn 322. The physical structure of the horn 322 may be arranged to transmit or otherwise convey ultrasonic vibration from the ultrasonic vibration generator 320 to the phacoemulsification needle 324. As shown in FIG. 3, the phacoemulsification needle 324 is disposed at the distal end 304 of the handpiece 112. A distal portion 326 of the phacoemulsification needle 324 forms a distal most tip of the handpiece 112, and is configured to emulsify tissue, such as a natural lens in a patient's eye, during a phacoemulsification procedure.

The irrigation system 310 provides irrigation fluid to the surgical site. The irrigation system 310 may include, for example, a fluidics fitting 330, an irrigation tube 332 connected to and extending from the fluidics fitting 330, an irrigation passage 334 formed or disposed within the body 302, and an irrigation sleeve 336. The fluidics fitting 330 may be a portion of a connector arranged to couple the irrigation system 310 to a fluid conduit connected to the fluidics subsystem 110 (shown in FIG. 2) at the surgical system 100. In some implementations, the fluidics fitting 330 is a quick-disconnect fitting that allows a user to readily connect and disconnect the handpiece 112 from the fluidics subsystem 110. In some implementations, the fluidics fitting 330 is a Luer fitting. Other implementations use other types of fittings. The irrigation tube 332 extends from the fluidics fitting 330 into the graspable body 302 and fluidically connects the irrigation passage 334 to the fluidics fitting 330. In the exemplary implementation shown, a portion of the irrigation tube 332 is disposed external of the handpiece body 302. Other implementations have an irrigation tube formed within the graspable body 302. In the exemplary implementation shown, the irrigation passage 334 is a cavity formed within the graspable body 302. In other implementations, the irrigation passage 334 may be formed of one or more tubes or conduits having a lumen that may be disposed within the graspable body 302.

The irrigation sleeve 336 may be in fluid communication with the irrigation passage 334 and, in the implementation shown, is arranged substantially coaxially about the phacoemulsification needle 324. Irrigation fluid flowing through the irrigation passage 334 may be directed into the irrigation sleeve 336 for passage to its tip 337, which is shown adjacent the distal portion 326 of the phacoemulsification needle 324. Accordingly, as the phacoemulsification needle 324 emulsifies tissue, irrigation fluid flows out of the tip 337 of the irrigation sleeve 336 to the surgical site. In some instances, one or more openings are formed through the sidewall of the sleeve 336 near the tip 337. The openings are in addition to the distal opening formed in the sleeve 336 through which the needle 324 extends from the sleeve 336. The openings permit irrigation fluid to exit the sleeve 336 and into the eye, for example, during a surgical procedure. The irrigation sleeve 336 may be removably attached to the graspable body 302 or may be permanently affixed to the graspable body 302. In the implementation shown, the irrigation sleeve 336 may be received over the phacoemulsification needle 324 and threaded onto the graspable body 302 to form a portion of the distal end 304 of the handpiece 112.

The aspiration system 312 may include an aspiration conduit 340, an impeller pump 342 having a pump motor 344, and an aspiration fitting 346. In the implementation shown, the aspiration conduit 340 may be defined by a lumen through the phacoemulsification needle 324 and the horn 322. The aspiration conduit 340 may convey aspiration fluid and emulsified or fragmented tissue from the surgical site to the impeller pump 342. In other implementations, the aspiration conduit 340 may be formed of an independent aspiration tube or conduit disposed adjacent to, but not defined by, the phacoemulsification needle 324 and the horn 322. In the exemplary implementation shown, an additional flow tube 348 extends from the aspiration conduit 340 in the horn 322 to the impeller pump 342 fluidically coupling the aspiration conduit 340 to the impeller pump 342.

The impeller pump 342 is structurally arranged to create low pressure in the aspiration conduit 340 in order to aspirate fluid and emulsified or fragmented tissue from the surgical site. The impeller pump 342 draws fluid from the aspiration conduit 340 and directs the fluid to the aspiration fitting 346. In the implementation shown, the aspiration fitting 346 connects directly to the graspable body 302 and extends at an angle therefrom for connection to a fluid conduit that extends to the base housing 102 (as shown in FIG. 2) or to a waste reservoir (not shown) disposed elsewhere. Like the fluidics fitting 330, the aspiration fitting 346 may be any connector arranged to fluidly connect to a fluid conduit. The aspiration fitting 346 may be selectively detachable from a fluid conduit via any type of fitting including a quick-disconnect fitting, and, in some instances, the aspiration fitting 346 may include a Luer fitting.

Figure 4:
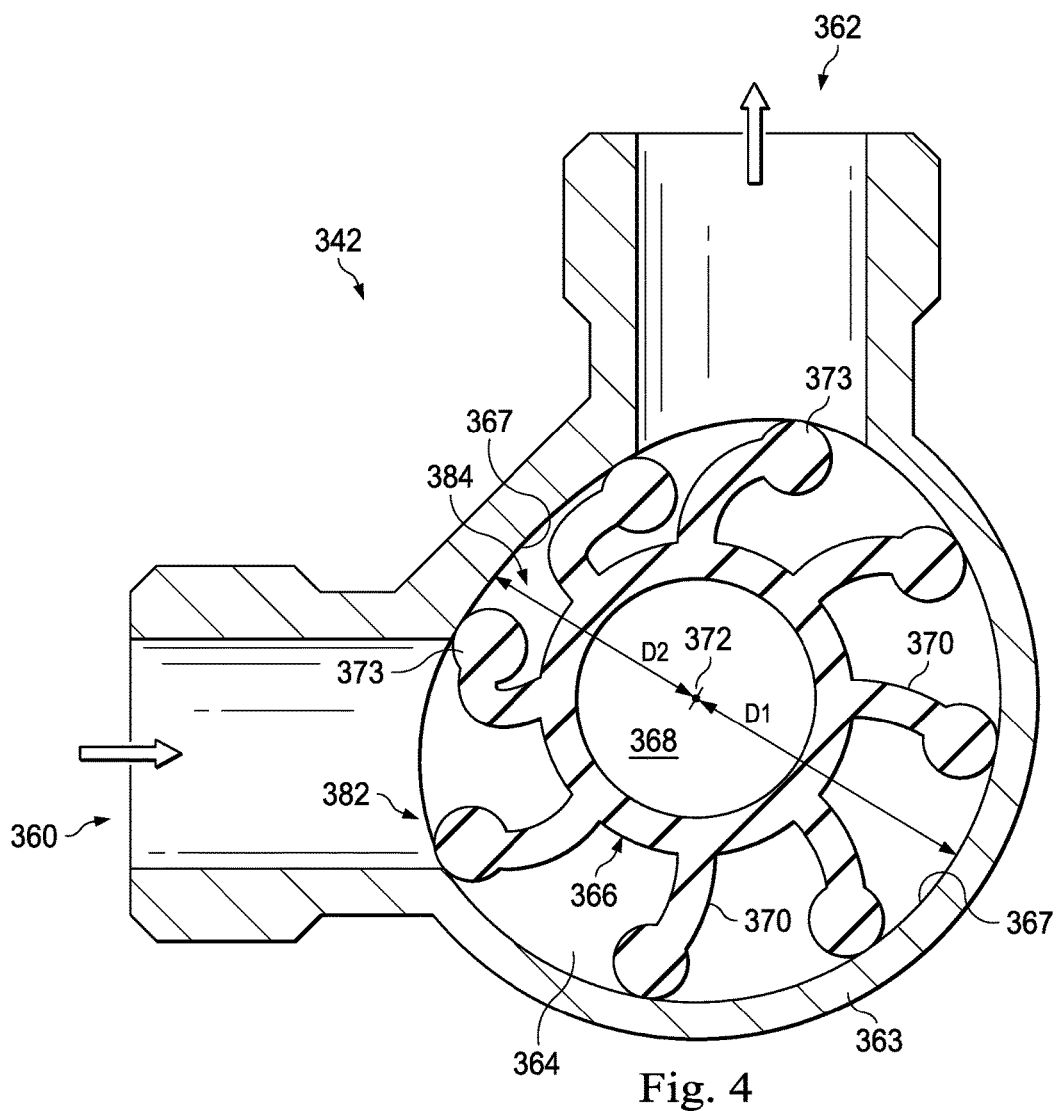
FIG. 4 is an illustration of a cross-sectional plan view of a flexible impeller pump forming a part of the surgical instrument of FIG. 3.

FIG. 4 shows an exemplary implementation of the impeller pump 342. As can be seen, the impeller pump 342 includes an inlet 360, an outlet 362, a housing 363 defining an impeller chamber 364, and a flexible impeller 366 disposed in the impeller chamber 364. The inlet 360 may be arranged to fluidically communicate with the aspiration conduit 340 in the handpiece 112, as shown in FIG. 3. Accordingly, the inlet 360 receives fluid and tissue from the surgical site. The outlet 362 is arranged to fluidically communicate with the aspiration fitting 346 and to direct the fluid and tissue away from the handpiece 112 for disposal. The impeller chamber 364 is defined by the housing 363 and disposed between and in fluid communication with the inlet 360 and the outlet 362. In the implementation shown, the inlet 360 and the outlet 362 are radially offset 90 degrees from each other. In some implementations, the inlet and the outlet may be radially offset by other angles relative to the impeller chamber 364. For example, in some implementations, the inlet and the outlet may be radially offset by an angle between 30 and 120 degrees. In other implementations, the inlet and the outlet are radially offset by an angle higher than 120 degrees or lower than 30 degrees.

The housing 363 includes an inner wall 367 that defines the boundaries of the impeller chamber 364. The flexible impeller 366 is disposed within the impeller chamber 364. In the exemplary implementation shown, the impeller chamber 364 is a noncircular chamber having a non-circular cross-section taken along a plane that is perpendicular to a rotation axis 372. The flexible impeller 366 is disposed non-concentrically within the impeller chamber 364.

Figure 5:
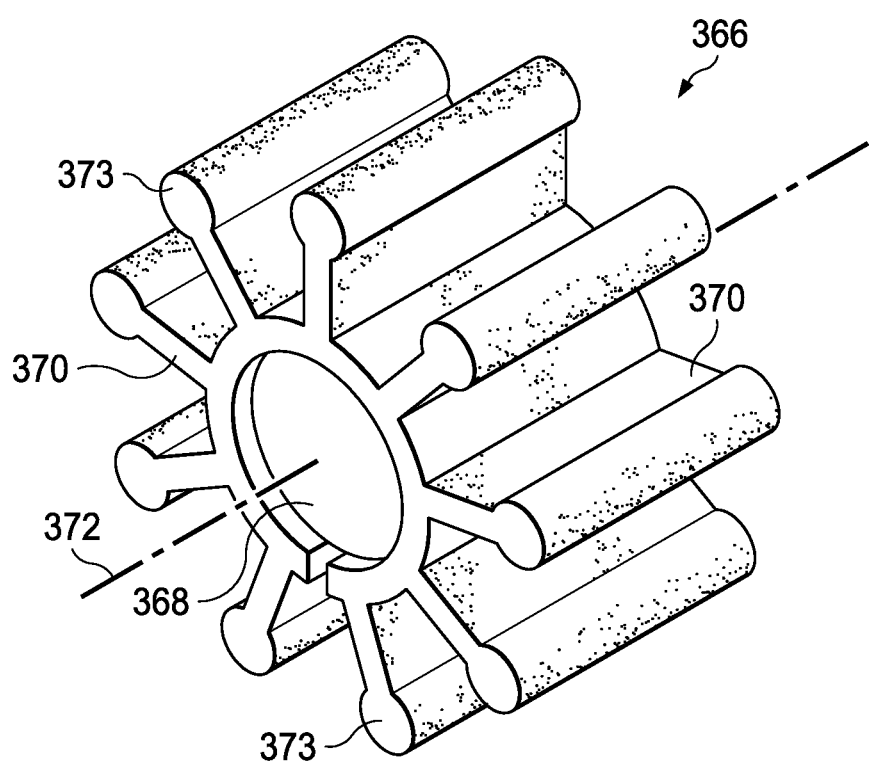
FIG. 5 is an illustration of a perspective view of an impeller usable in the impeller pump of FIG. 4.

The flexible impeller 366 is shown in FIGS. 4 and 5. The flexible impeller 366 includes a hub 368 and radially extending vanes 370. The hub 368 is arranged to pivot around the rotation axis 372, shown as a single point in FIG. 4. Because of the noncircular shape of the impeller chamber 364, the flexible impeller 366 is disposed closer to one portion of the inner wall 367 than another portion of the inner wall 367, or, in other words, the flexible impeller 366 is offset from a center of the impeller chamber 364. This divides the impeller chamber 364 into a fluid high flow portion 382 and a fluid low flow portion 384. For example, the distance from the rotation axis 372 to the inner wall 367 adjacent the fluid high flow portion 382 is a distance D1 in FIG. 4, and is greater than a distance D2 from the rotation axis 372 to inner wall 167 adjacent the low flow portion 384. This type of an offset causes deflection of the vanes 370 passing through the low flow portion 384, minimizing the carried fluid volume. In contrast, the vanes 370 passing through the high flow portion 382 are less deflected, permitting a much greater carried fluid volume. This provides fluid flow primarily in one direction, from the inlet 360 to the outlet 362 when the flexible impeller 366 rotates in the counter-clockwise direction.

The vanes 370 extend radially outwardly from the hub 368. In the example shown, the vanes 370 are spaced apart to drive fluid from the inlet 360 toward the outlet 362. The exemplary flexible impeller shown includes eight vanes, with the vanes radially spaced every 45 degrees. The number of vanes and the radial spacing may be dependent on the size of the inlet and the outlet. In some implementations, adjacent vanes may be radially spaced within a range of 30 and 70 degrees. In some implementations, adjacent vanes may be radially spaced within a range of about 30 degrees and 120 degrees. However, in other implementations, the number of vanes 370 and the angular spacing therebetween may be selected to be any desired value.

In the implementation shown, each vane 370 includes a bulbous tip 373 that is arranged to contact and slide along the inner wall 367 of the impeller chamber 364 to drive the aspiration fluid and emulsified tissue toward the outlet 362. Other implementations do not include a bulbous tip at the ends of the vanes 370.

As can be understood from FIG. 4, the vanes 370 are formed of a flexible material. Because of this, the vanes 370 may flex or deform when the vanes 370 engage against the inner wall 367 defining the impeller chamber 364. They also may flex or deform when brought into contact with fragmented tissue. Because of this, the flexible impeller 366 may be well-suited to maintain satisfactory operation when fragmented tissue may become lodged between the inner wall 367 and one or more vanes 370. Particularly, the vanes 370 may deflect to accommodate the fragmentation without jamming or otherwise disrupting the ability of the flexible impeller 366 to rotate. The impeller pump 342 may be arranged to provide pumping action of fluid and tissue even when the tissue particulates are large or abnormally shaped. The vanes 370 may be formed of any flexible material, including, for example, and without limitation, silicon, rubber, or other flexible material. Because the vanes 370 of the flexible impeller pump 342 can flex or deflect to accommodate tissue fragments lodged between the vanes 342 and the inner wall 367 of the impeller chamber 364, the pump rotation speed is largely unaffected and the vanes 370 will continue to move and advance the tissue toward the pump outlet 362.

In some implementations, the flexible impeller 366 may be removable from the impeller pump 342 and/or the handpiece 112. For example, in some implementations, the graspable body 302 may include an access port 374, shown in FIG. 3, that provides access into an interior of the graspable body 302 and to the impeller housing 363. After each use, the handpiece 112 may be sterilized, and a new flexible impeller may replace the used flexible impeller.

In the example handpiece 112 illustrated in FIG. 3, the pump motor 344 is disposed at a location proximal of the location of the impeller pump 342. The arrangement of the pump motor 344 and the impeller pump 342, though, may be different in other implementations. The pump motor 344 is arranged to rotate the flexible impeller 366 to provide an aspiration flow from the surgical site. In some implementations, the pump motor 344 comprises a shaft on which the flexible impeller 366 resides. In other implementations, the pump motor 344 drives a transmission or gear chain that drives the flexible impeller 366. In the exemplary implementation shown, the pump motor 344 is disposed within the graspable body 302. Other implementations include the pump motor 344 external of the graspable body 302, or otherwise carried by the graspable body 302.

In some implementations, the pump motor 344 may be a variable speed motor controlled by the control system 103 of the surgical system 100. In some implementations, the pump motor 344 may be reversible, and because of the flexible vanes 370, the flexible impeller 366 is able to reverse flow to reflux. The reflux may be effective to clear the phacoemulsification needle from occlusions. Responsive to pump control signals generated at the control system 103, the pump motor 344 may increase flow, decrease flow, or maintain flow at a desired flow rate based on a measured or calculated parameter indicative of pressure at the surgical site. Consistent with this, in some implementations, the handpiece 112 may include a sensor 392 associated with the aspiration system 312. In some exemplary implementations, the sensor 392 may be located along the aspiration conduit 340 or located near the distal end 304 and in fluid communication with the surgical site. In some implementations, the sensor 392 may be located within the surgical site and in communication with a controller forming a part of the fluidics subsystem 110. In some implementations, the sensor 392 detects a pressure at the surgical site or a pressure associated with the surgical site.

In some implementations, the sensor 392 is in communication with the control system 103 on the surgical system 100. The control system 103 may be configured to receive information from the sensor 392, such as pressure information, which may be indicative of IOP. The control system 103 may include an executable program for operating the pump motor 344 of the impeller pump 342. The control system 103 may receive inputs from an operator or may include pre-stored optimum targets for the aspiration flow. These target and received inputs may be a single value or a range of values. In some implementations, the control system 103 includes a PID controller configured to control the impeller pump to mitigate pressure deviations.

The control system 103 may be in communication with and may be configured to control the operation of the impeller pump 342. In operation, the pump motor 344 rotates the flexible impeller 366. The control system 103 may control the operation of the pump motor 344. In this manner, the flexible impeller 366 may be rotated at any desired speed to produce any desired aspiration flow rate. When rotated, the impeller pump 342 draws the aspiration fluid 385 through the aspiration conduit 340. The control system 103 may use the pressure information received from the sensor 392 to determine whether the speed of the impeller pump 342 should be increased or decreased to maintain or regulate IOP.

In the exemplary implementation shown in FIG. 3, the sensor 392 is located along the aspiration conduit 340 between the impeller pump 342 and the distal end 304. In this manner, the sensor 392 can accurately detect the pressure conditions in the aspiration conduit 340 very close to the surgical site. Detecting pressure conditions close to the surgical site may result in early detection of occlusion breaks, and therefore, may reduce the change or impact of occlusion surges.

The control system 103, may detect pressure deviations in the system, such as those that may occur as a result of an occlusion in the aspiration system, and may quickly act to counter the effects of any occlusion surge. For example, the control system 103 may use the changes in pressure within an aspiration conduit, such aspiration conduit 340, detected by the sensor, such as, for example, sensor 392, to detect an occlusion, such as an occluded tip. Upon detecting an occlusion (based on the pressure readings from the sensor), the control system 103 may adjust the aspiration flow using the flexible impeller pump to reduce the effects of a post-occlusion surge. The continuous monitoring of the pressure within the aspiration conduit may result in a more consistent and predictable phacoemulsification procedure by reducing the effects of pressure deviations that occur with post-occlusion surges, that is, by immediately responding to the deviations in pressure. For example, data representing the pressure level within the aspiration conduit may be transmitted to the control system 103. The control system 103 may detect an occlusion when the pressure within the aspiration conduit begins to drop below a selected level. This drop in pressure beyond the selected level may be a buildup of vacuum pressure within the aspiration conduit. In response to this reduction in pressure, the control system 103 may alter a speed of an aspiration pump, such as impeller pump 342, in order to reduce the amount of vacuum generated within the aspiration line. A reduction in the vacuum pressure may reduce or eliminate post-occlusion surge once the occlusion clears.

In conventional phacoemulsification systems, the pump is located within apart from a handpiece, such as within a surgical console. A relatively long length of flexible conduit (six feet or more) is located between an aspiration and irrigation pump and the eye. This relatively long length of flexible conduit has high compliance. That is, the compliance of flexible conduit causes the flexible conduit to change dimensions and contract in response to changes in vacuum pressure. This compliance can result in surges as previously described. By incorporating the pump that interfaces with the aspiration conduit in the handpiece 112 (and placing the pump very close to the eye) and having a very short length of conduit between the impeller pump 342 and the eye, the effects of these surges can be reduced or eliminated, thus resulting in a more consistent and predictable surgery. Furthermore, using a flexible impeller may create additional efficiencies and reduce the impact of fragments that disrupt pump flow of conventional pumps.

Persons of ordinary skill in the art will appreciate that the implementations encompassed by the present disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A phacoemulsification system comprising:
a hand-graspable body;
a phacoemulsification needle extending from a distal portion of the body and arranged to ultrasonically vibrate to treat an ocular condition;
an ultrasonic vibration generator cooperatively coupled to the phacoemulsification needle, the phacoemulsification needle ultrasonically vibratable in response to a vibration of the ultrasonic vibration generator; and
an impeller pump carried by the hand-graspable body and configured to convey an aspiration fluid from a surgical site, the impeller pump comprising:
an aspiration motor, and
a flexible impeller coupled to and rotatably driven by the aspiration motor, the flexible impeller being arranged to aspirate fluid and emulsified lens tissue from the surgical site, wherein the impeller pump comprises an impeller chamber, the impeller being non-concentrically disposed within the impeller chamber.

2. The phacoemulsification system of claim 1, wherein the flexible impeller comprises a plurality of radially extending vanes.

3. The phacoemulsification system of claim 2, wherein each of the plurality of radially extending vanes comprises a bulbous tip.

4. The phacoemulsification system of claim 2, wherein the vanes are radially spaced apart within a range of 30 and 70 degrees.

5. The phacoemulsification system of claim 1, wherein the impeller chamber has a non-circular cross-section.

6. The phacoemulsification system of claim 1, wherein the impeller chamber comprises an inlet and an outlet extending at an angle from each other, the angle being between 30 and 120 degrees.

7. The phacoemulsification system of claim 1, further comprising an access opening that provides selective access to the impeller pump.

8. The phacoemulsification system of claim 7, wherein the flexible impeller is removable from the body through the access opening.

9. The phacoemulsification system of claim 1, wherein the impeller pump comprises an inlet in fluid communication with the needle and an outlet in fluid communication with a connector disposed on the hand-graspable body.

10. The phacoemulsification system of claim 1, further comprising:
a sensor carried on the hand-graspable body; and
a controller in communication with the sensor and configured to generate a pump control signal to control the impeller pump based on information sensed by the sensor.

11. A phacoemulsification system for treating an ocular condition at a surgical site, comprising:
a hand-graspable body;

an irrigation system carried on the hand-graspable body and configured to convey an irrigation fluid for injection from a distal end of the hand-graspable body to the surgical site; and an aspiration system carried on the hand-graspable body and configured to convey an aspiration fluid into the distal end of the hand-graspable body from the surgical site, the aspiration system comprising:

an aspiration motor, an impeller chamber, and a flexible impeller rotatably disposed in the impeller chamber and coupled to and rotatably driven by the aspiration motor, the flexible impeller being arranged to aspirate fluid and emulsified lens tissue from the surgical site, wherein the impeller chamber has a non-circular cross-section.

12. The phacoemulsification system of claim 11, further comprising:

a phacoemulsification needle extending from the distal portion of the body and arranged to ultrasonically vibrate to treat the ocular condition; and an ultrasonic vibration generator cooperatively coupled to and arranged to vibrate the phacoemulsification needle.

13. The phacoemulsification system of claim 11, wherein the flexible impeller comprises a plurality of radially extending vanes.

14. The phacoemulsification system of claim 13, wherein each of the plurality of radially extending vanes comprises a bulbous tip.

15. The phacoemulsification system of claim 13, wherein the vanes are radially spaced apart within a range of 30 and 70 degrees.

16. The phacoemulsification system of claim 11, comprising:

a sensor carried on the hand-graspable body; and a controller in communication with the sensor and configured to generate a pump control signal to control the aspiration motor based on information sensed by the sensor.

* * * * *